United States Patent [19]

Howson et al.

[11] Patent Number: 4,846,797

[45] Date of Patent: Jul. 11, 1989

[54] SYRINGE POSITIONING DEVICE FOR ENHANCING FLUID FLOW CONTROL

[75] Inventors: David C. Howson, Denver; Michael W. Fellinger, Boulder; John A. Popken, Longmont; Richard M. Altobellis, Lyons; all of Colo.

[73] Assignee: Intelligent Medicine, Inc., Englewood, Colo.

[21] Appl. No.: 142,126

[22] Filed: Jan. 11, 1988

Related U.S. Application Data

[62] Division of Ser. No. 734,028, May 14, 1985.

[51] Int. Cl.$^4$ .............................................. A61M 5/20
[52] U.S. Cl. .............................. 604/154; 128/DIG. 1; 128/DIG. 12
[58] Field of Search ................. 604/65, 131, 151, 154, 604/155, 207, 246; 128/DIG. 1, DIG. 12

[56] References Cited

U.S. PATENT DOCUMENTS

| | | | |
|---|---|---|---|
| 2,734,504 | 2/1956 | Crescas et al. | 128/DIG. 1 |
| 2,786,468 | 3/1957 | Singer et al. | 604/155 |
| 3,156,236 | 11/1964 | Williamson | 128/DIG. 1 |
| 3,266,299 | 8/1966 | Swank | 128/DIG. 1 |
| 4,255,096 | 3/1981 | Coker, Jr. et al. | 128/DIG. 1 |
| 4,465,475 | 8/1984 | Mardorf et al. | 604/155 |
| 4,544,369 | 10/1985 | Skakoon et al. | 604/155 |
| 4,620,848 | 11/1986 | Sutherland et al. | 604/154 |
| 4,695,271 | 9/1987 | Goethel | 128/DIG. 1 |

FOREIGN PATENT DOCUMENTS

| | | | |
|---|---|---|---|
| 0092712 | 11/1983 | European Pat. Off. | 604/131 |
| 2125487 | 3/1984 | United Kingdom | 604/131 |

OTHER PUBLICATIONS

Cordis Corporation, Miami, Fla. Cat. No. 404-100, 404-102, 1972.

Primary Examiner—Stephen C. Pellegrino
Assistant Examiner—Ralph Lewis
Attorney, Agent, or Firm—Robert E. Harris

[57] ABSTRACT

A syringe positioning device is disclosed for enhancing control of fluid flow from a syringe. A disposable unit that includes a syringe and rack mounted on a retaining clip is positionable on a drive unit so that, when so positioned, the piston of the syringe is precisely displaced to deliver medicament from the syringe to a patient. A non-disposable unit is also disclosed onto which a syringe and piston can be positioned so that the device thereafter also provides precise medicament delivery. The longitudinal movement of the rack is effected by rotating the pinion gear that is connected with a pulse-driven, power efficient stepper motor, with the operation of the stepper motor being controlled by a pre-programmed memory unit. A hinged rack is also disclosed, as is a one-way ball drive unit.

20 Claims, 9 Drawing Sheets

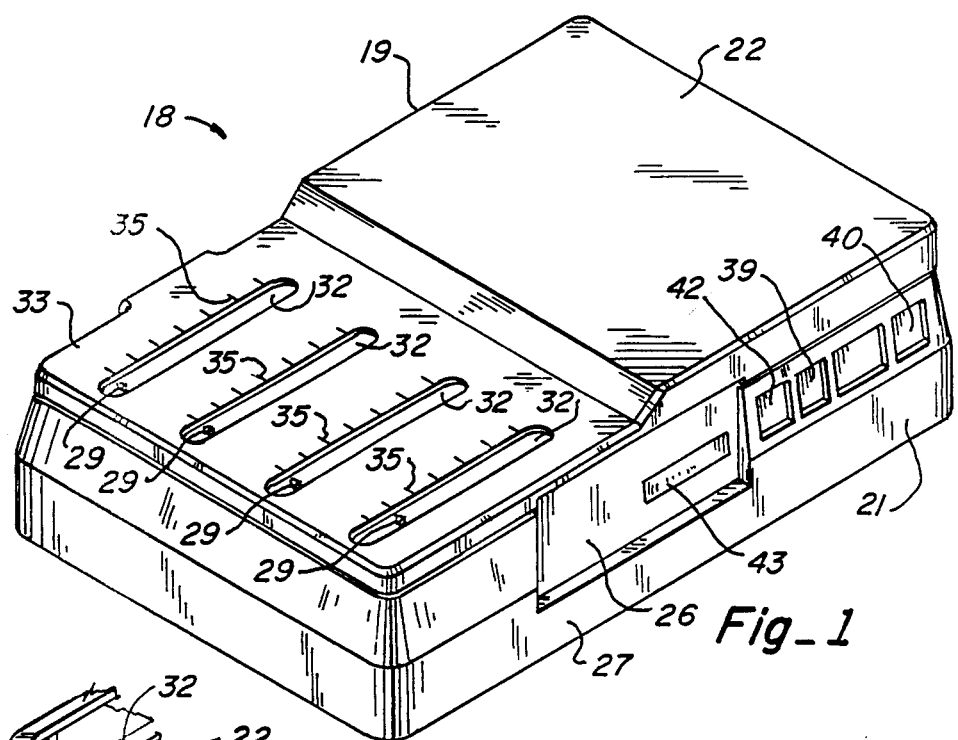
Fig_1
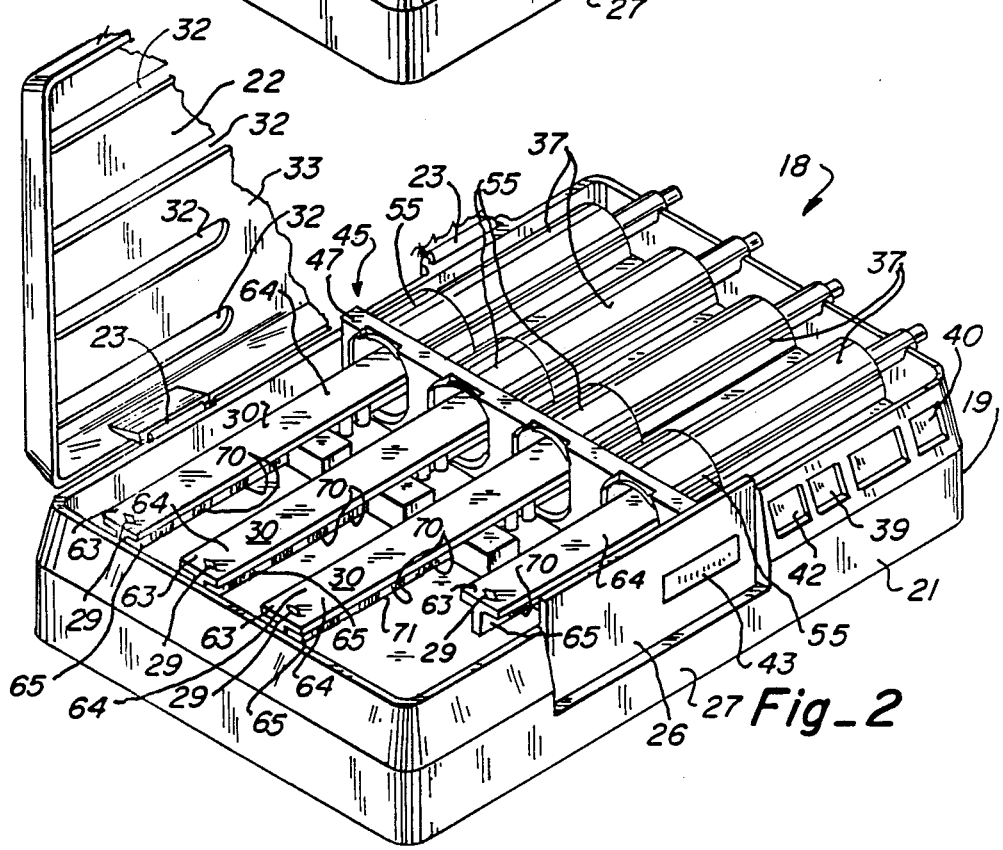
Fig_2

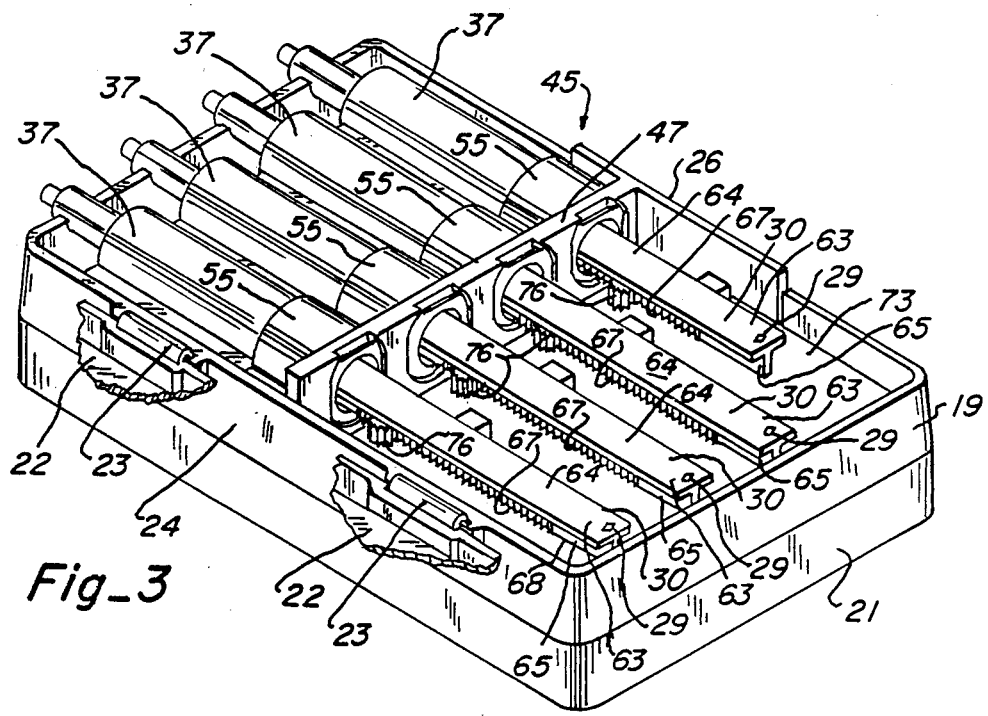
Fig_3
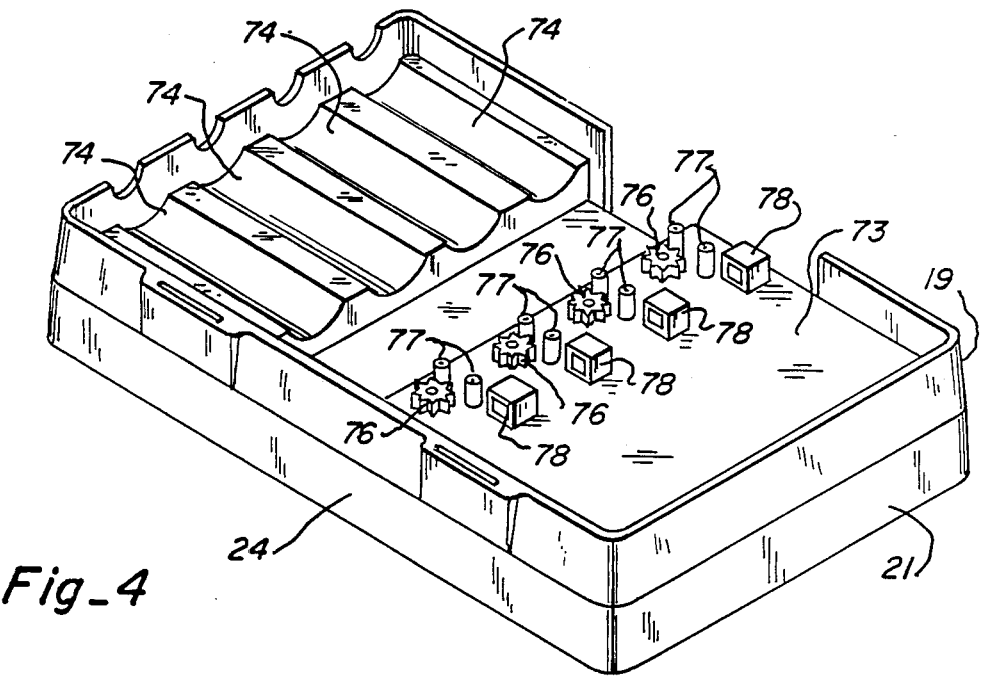
Fig_4

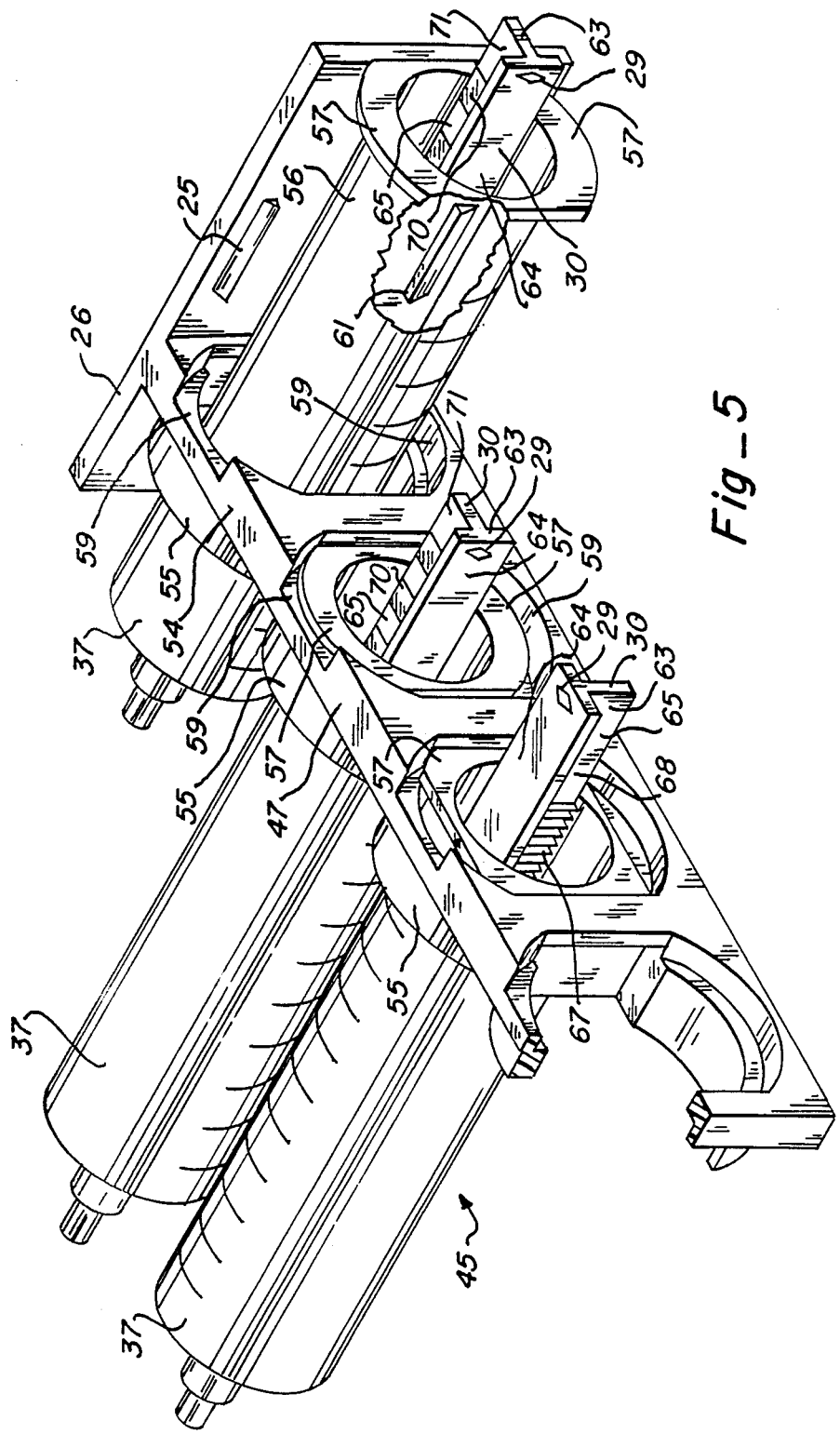
Fig_5

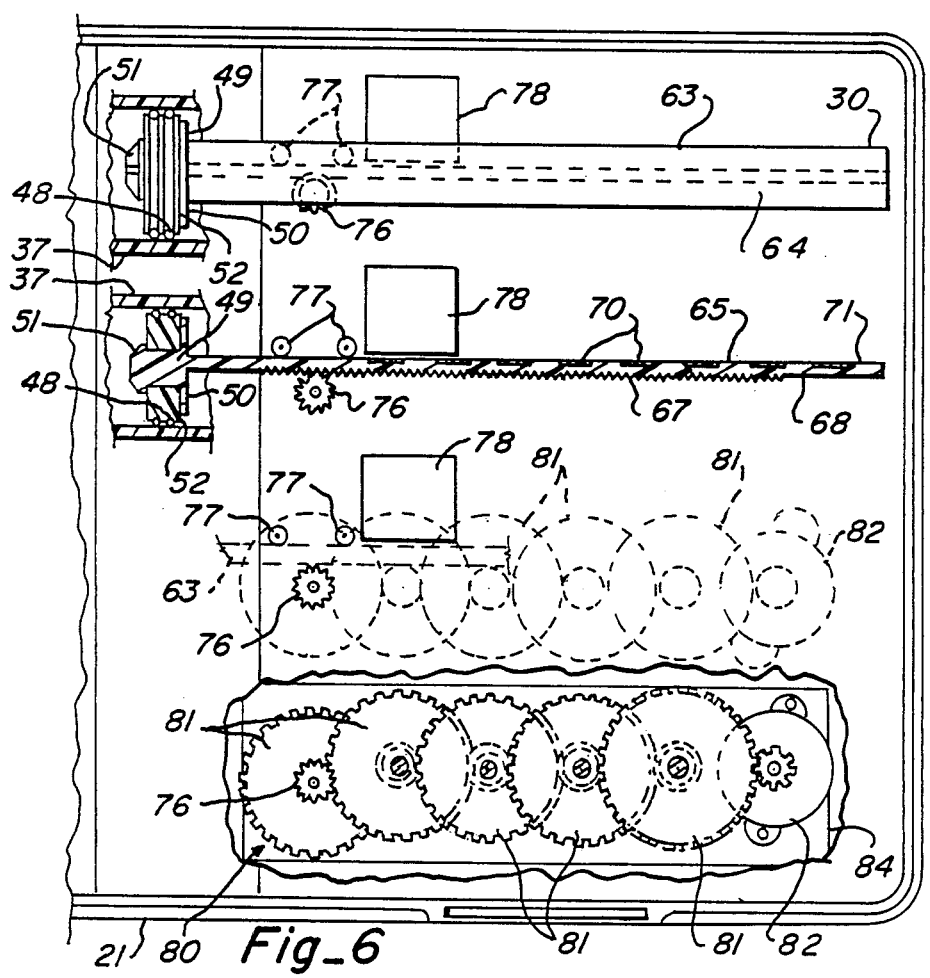
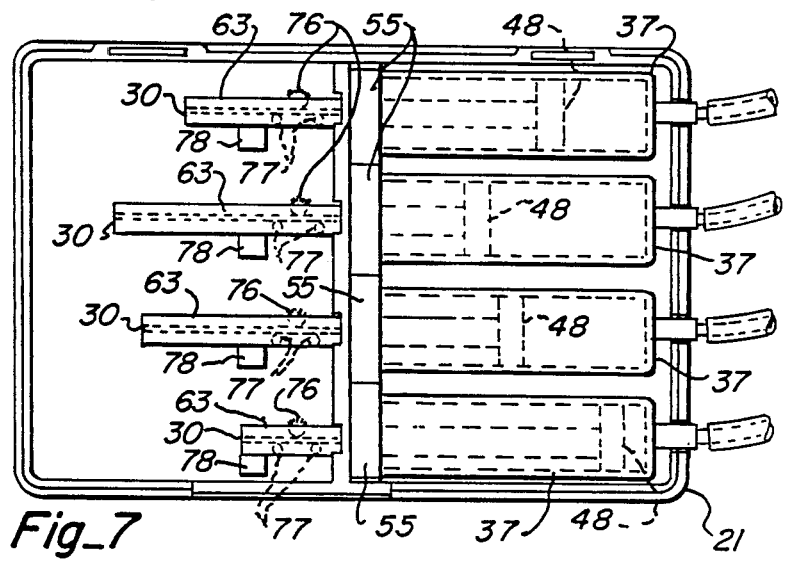

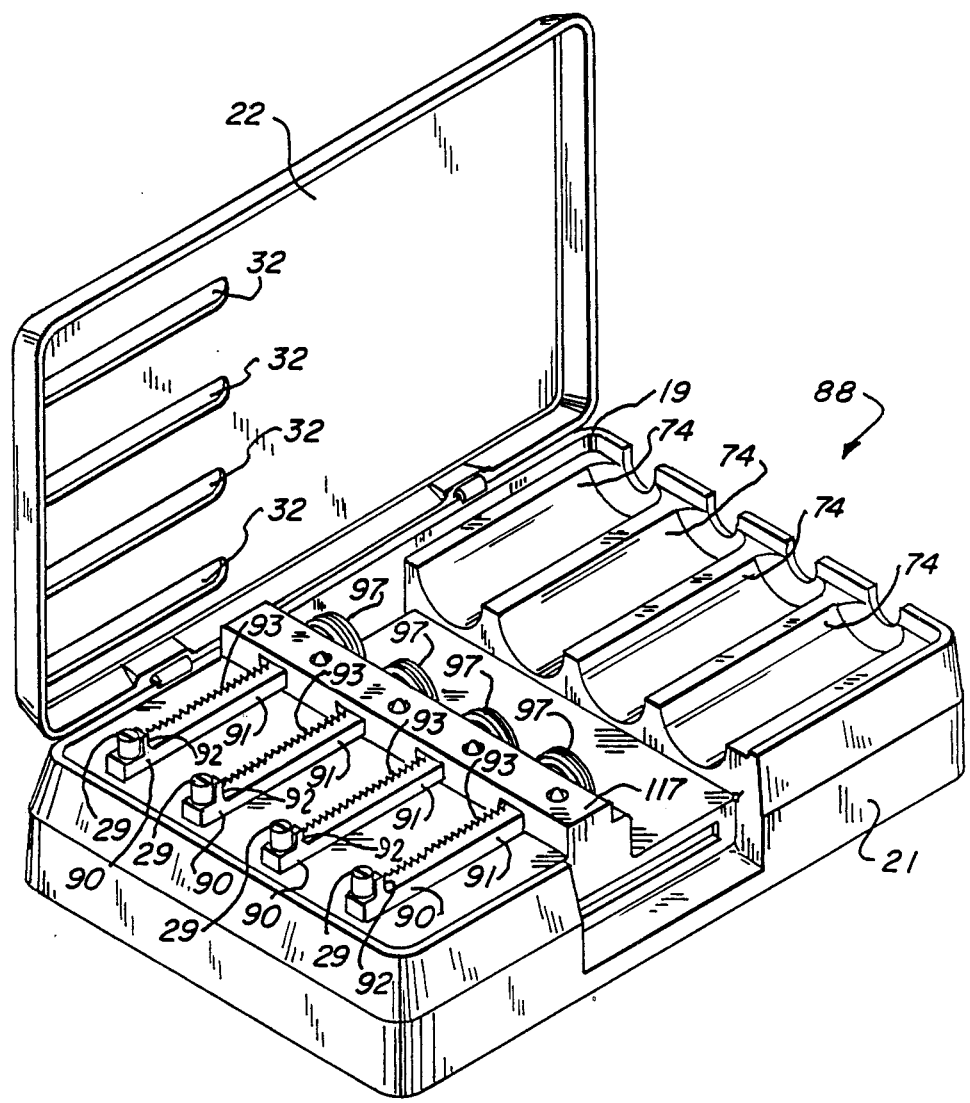
Fig_8

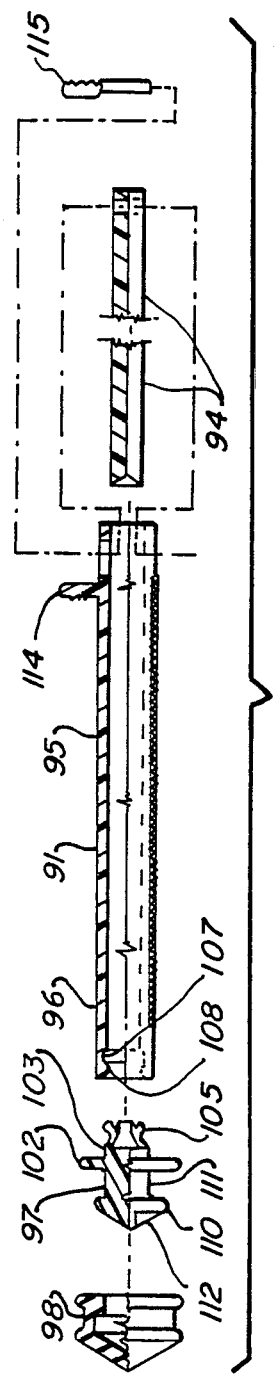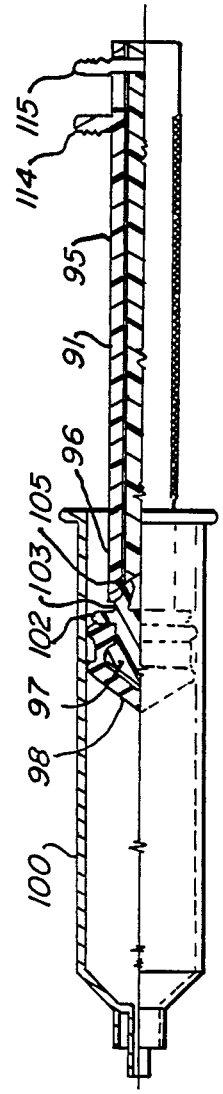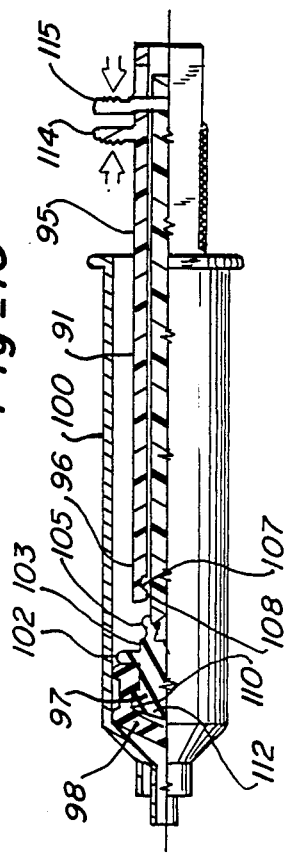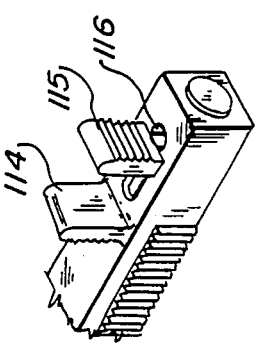
Fig_9  Fig_10  Fig_11  Fig_10A

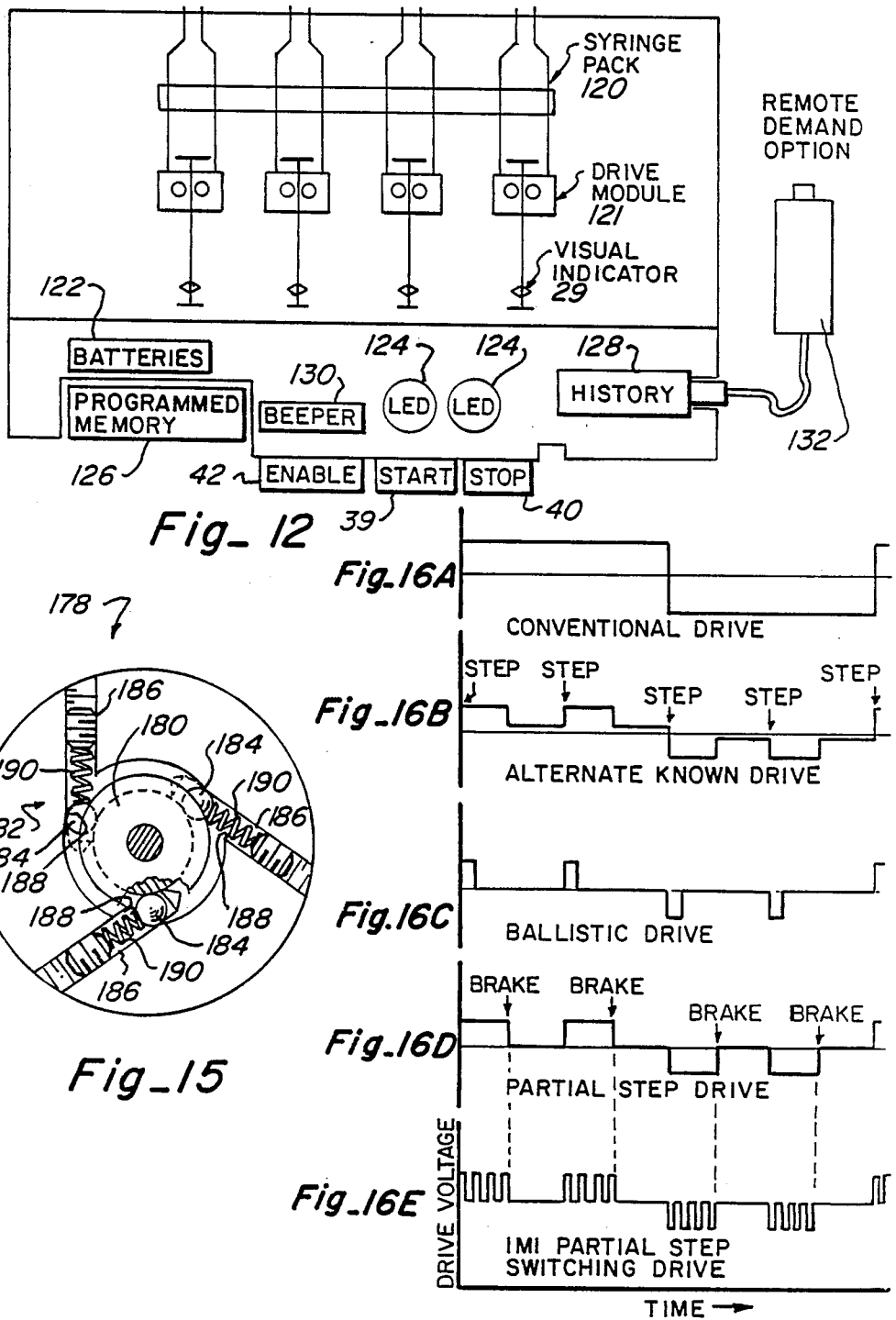

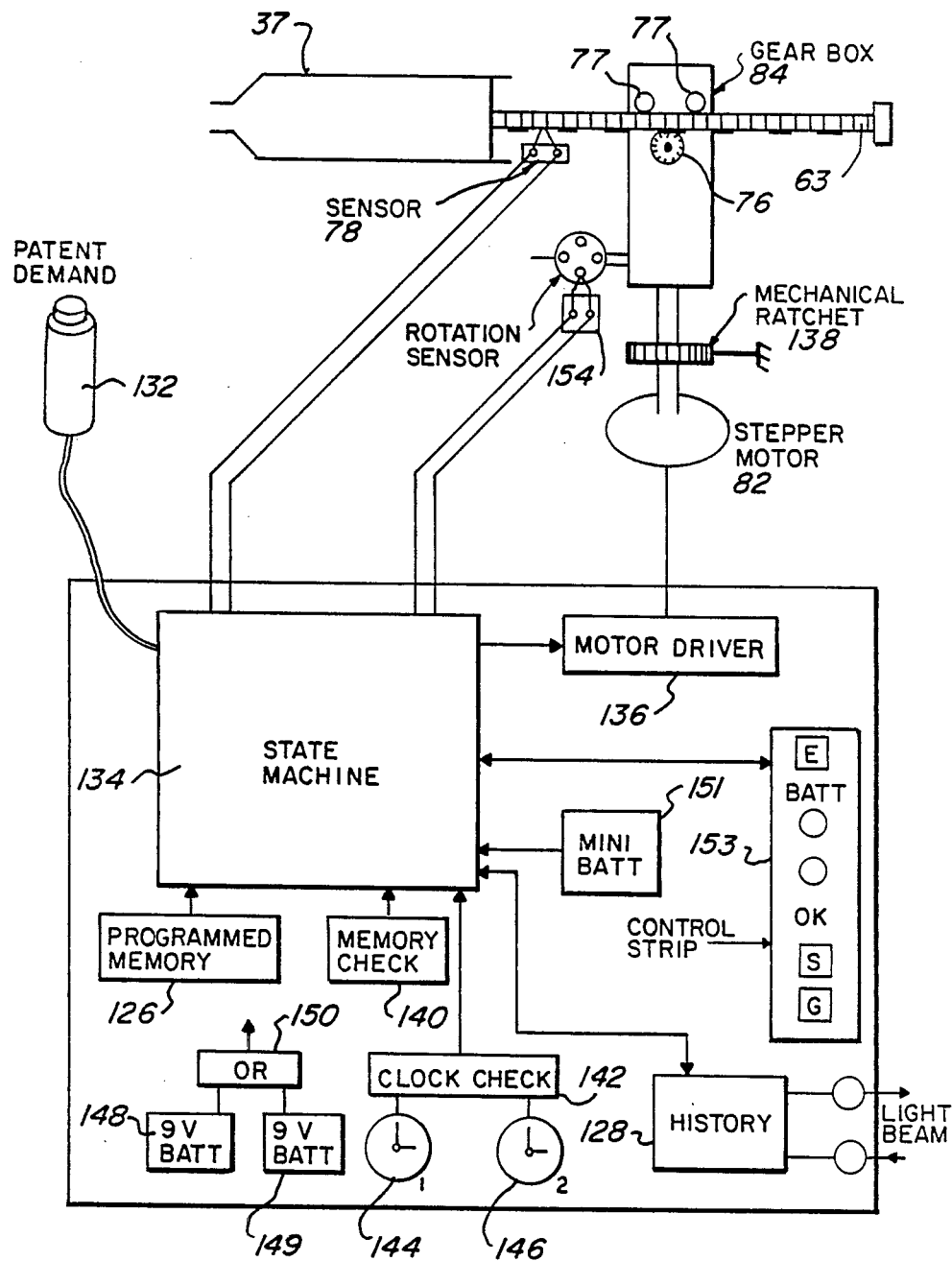
Fig_13

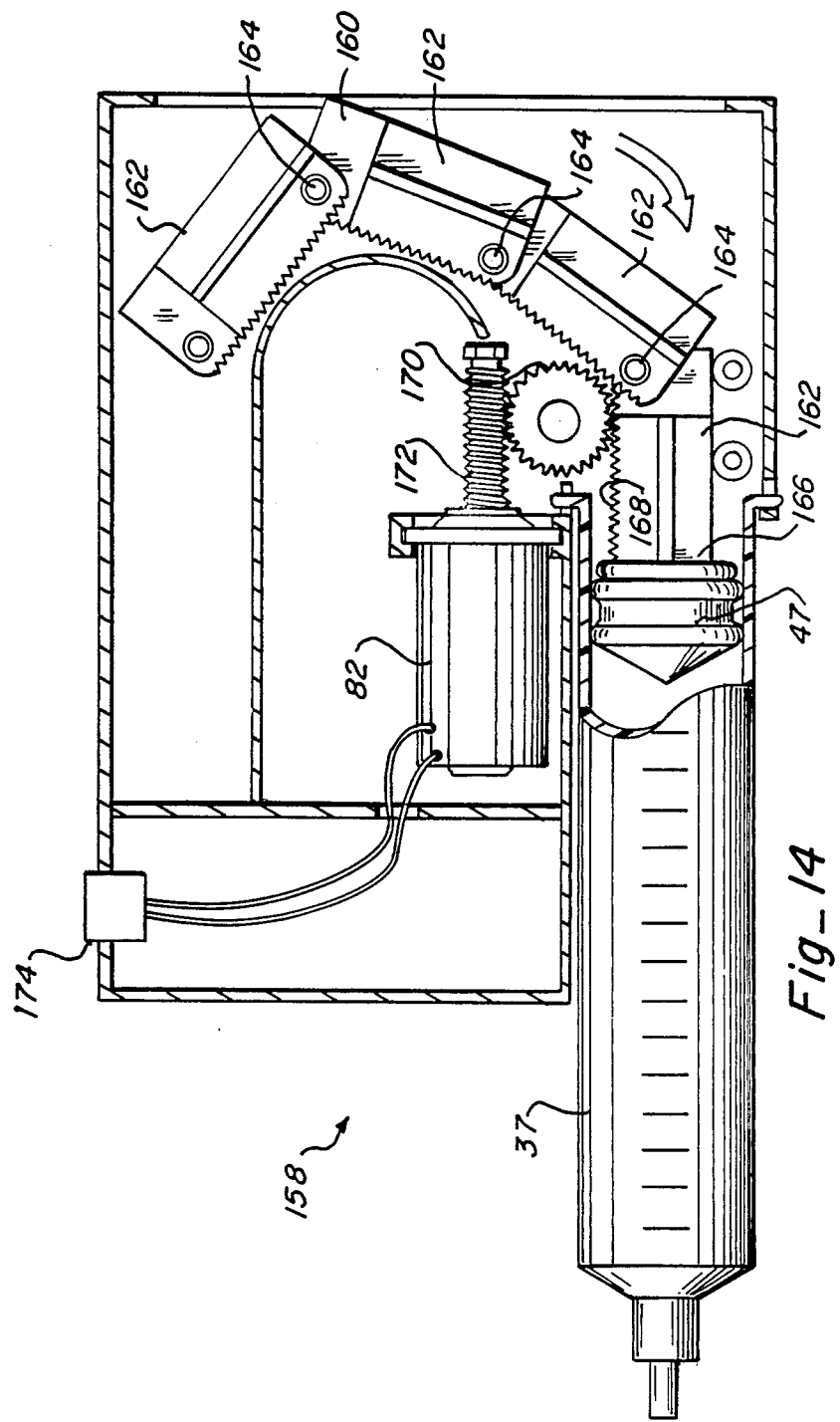

SYRINGE POSITIONING DEVICE FOR ENHANCING FLUID FLOW CONTROL

RELATED APPLICATION

This application is a Division of our copending application Ser. No. 734,028 filed on May 14, 1985 and entitled "Syringe Drive Apparatus And Method".

FIELD OF THE INVENTION

This invention relates to a positioning device, and, more particularly, relates to a syringe positioning device for enhancing fluid flow control.

BACKGROUND OF THE INVENTION

The use of syringes to retain a fluid, such as a medicament, is well known. Devices including syringe positioning apparatus have also been heretofore suggested and/or utilized to control delivery of medicament from the syringe by controlling the movement of the syringe piston (see for example U.S. Pat. Nos. 4,255,096 and 2,764,980).

Prior devices for controlling movement of the syringe piston have, however, not proved to be fully effective, at least for all intended purposes. Some prior known devices have, for example, lacked simplicity of structure and/or operation, have not provided for ease of interchange of disposable elements, have been ineffective in precisely controlling medicament delivery, have lacked the ability to deliver changing amounts of medicament over different time periods, have lacked safeguards against undesired use, and/or have not been fully dependable in operation.

SUMMARY OF THE INVENTION

This invention provides an improved syringe positioning device for enhancing control of delivery of fluid from a syringe. In the preferred embodiment, precise delivery of fluid from the syringe is effected using a disposable unit insertable into a drive unit, with the disposable unit including both the syringe and a rack mounted on a retaining clip. A non-disposable unit is also shown for effecting precise delivery of fluid from a syringe and piston unit insertable into a drive unit having a rack and pinion provided therein.

It is therefore an object of this invention to provide an improved device for enhancing control of delivery of fluid from a syringe.

It is still another object of this invention to provide an improved device for controlling delivery of fluid from a syringe utilizing a disposable unit.

It is yet another object of this invention to provide a retaining device for precisely positioning an object adjacent to a structure.

It is still another object of this invention to provide a retaining device for precise positioning of an object adjacent to a base structure having a drive element engageable with a portion of the object which includes a mounting portion having a mounting station for receiving the object, a locking portion for precluding movement of the object relative to the mounting portion, and a fastener for releasable connecting the mounting portion to the base structure at a predetermined position.

It is still another object of this invention to provide an improved device for controlling delivery of fluid from a syringe utilizing a disposable unit with a syringe and rack retained by a retaining clip.

It is yet another object of this invention to provide a disposable unit for operably positioning a plurality of syringes in a fluid delivery control device, the disposable unit including a mounting wall having a plurality of barrels extending therefrom, a bracket configured for releasable attachment of the mounting wall to the control device, and locking apparatus for releasably securing the syringes in the barrels of the mounting wall.

With these and other objects in view, which will become apparent to one skilled in the art as the description proceeds, this invention resides in the novel construction, combination, and arrangement of parts substantially as hereinafter described and more particularly defined by the appended claims, it being understood that changes are meant to be included as come within the scope of the claims.

DESCRIPTION OF THE DRAWINGS

The accompanying drawings illustrate complete embodiments of the invention according to the best mode so far devised for the practical application of the principles thereof, and in which:

FIG. 1 is a perspective view of the syringe drive device of this invention shown with the protective casing in the closed position;

FIG. 2 is a partial front perspective view of the disposable syringe drive device of this invention shown with the protective casing in the open position and illustrating the disposable syringe assembly operatively placed within the casing;

FIG. 3 is a rear perspective view of the syringe drive device shown in FIG. 2 with the lid cut away for illustrative purposes;

FIG. 4 is a top perspective view of the syringe drive device as shown in FIG. 3 except that the disposable syringe assembly has been removed from the device;

FIG. 5 is a partial perspective view of the disposable syringe assembly shown in FIGS. 2 and 3 and illustrating the retaining clip locking feature;

FIG. 6 is a top view of the syringe drive device as shown in FIGS. 2 through 4 with various structures partially broken away to illustrate gearing for the rack and pinion drive assembly;

FIG. 7 is a top view of the syringe drive device with the lid removed and four syringes operatively positioned to illustrate different driven stages of the syringes;

FIG. 8 is a perspective view of the non-disposable syringe drive device of this invention shown with the protective cover in an open position and without syringes operatively positioned within the casing;

FIG. 9 is an exploded partial side view of the rack and connecting assembly for use with the non-disposable syringe device as shown in FIG. 8;

FIG. 10 is a partial side view of the rack and connecting assembly for use with the non-disposable syringe device as shown in FIG. 8 with the rack shown connected with the syringe piston;

FIG. 10(A) is a partial perspective view illustrating the rear section of the rack assembly;

FIG. 11 is a side view of the rack and connecting assembly as shown in FIG. 10 with the rack shown in position for releasing the piston;

FIG. 12 is a layout schematic of the syringe drive unit;

FIG. 13 is a layout schematic illustrating syringe drive and control;

FIG. 14 is a perspective view of an alternate embodiment of the syringe device using a hinged rack assembly;

FIG. 15 is an end view of another embodiment of the syringe drive device utilizing a one-way roller drive; and.

FIG. 16 (A) is a conventional drive timing pulse utilized to drive the stepper motor.

FIG. 16 (B) is an alternate known drive timing pulse utilized to drive the stepper motor.

FIG. 16 (C) is a ballistic drive timing pulse utilized to drive the stepper motor.

FIG. 16 (D) is a partial step drive timing pulse utilized to drive the stepper motor.

FIG. 16 (E) is an IMI Partial step switching drive timing pulse utilized to drive the stepper motor.

DESCRIPTION OF THE INVENTION

Referring now to the drawings, syringe drive 18 is shown in FIG. 1 within casing, or housing, 19. Casing 19, as best shown in FIGS. 1 through 4, includes a base, or bottom, portion 21 and a lid, or top, portion 22 that is hinged by hinges 23 at the rear side 24 of base portion 21. In addition, a retaining, or locking, mechanism 25 (see FIG. 5) is provided on mounting bracket 26 at the front side 27 of the base portion.

As best shown in FIGS. 1 through 3, a tab, or indicator, 29 is provided on rack 30 so as to be visible through the slotted openings 32 in the top 33 of lid 22. As shown in FIG. 1, indicia 35 are also preferably utilized at the side of each slotted opening 32 to indicate the amount of use of fluid dispensed from syringe 37 then being driven by rack 30.

As also indicated in FIGS. 1, 2, and 12, depressable start and stop buttons 39 and 40, respectively, are provided at front portion 27 of base portion 21 of the casing 19. In addition, a light emitting diode (LED) enable flasher indicator 42 is provided at base portion 21, and an information plate 43 is also provided at mounting bracket 26.

The now preferred embodiment of this invention is shown in FIGS. 2 through 7, and includes a disposable unit 45. Unit 45 includes syringe 37 and rack 30 both of which are mounted on retaining clip 47. Retaining clip 47 preferably receives and retains a plurality of syringes (four are indicated by way of example in FIGS. 1 through 7), and each syringe has a separate rack 30 connected with syringe piston, or plunger, 48 by means of connector 49 which receives centrally apertured piston 48 between disc 50 and end retainer 51 (see FIG. 6). Piston 48 has sealing lips 32 for engaging the inner surface of the syringe barrel, as is conventional.

As best shown in FIG. 5, retaining clip 47 includes a mounting wall 54 having a plurality of barrels 55 formed therein to receive the rear end portion 56 of each syringe. As also shown in FIG. 5, the rear end portion 56 of end syringe has arcuate lip portions 57 at opposite sides which are received in matching portions 59 of each clip barrel 55. After insertion and upon rotation (preferably about 90° of the syringe about its central axis), lip portion 57 rotates behind the end of the barrel, and is thereafter locked against movement with respect to the clip until the syringe is further rotated in either direction, so that the lips are again aligned with the matching arcuate portions of the barrel.

Mounting bracket 26 is attached to wall 54 and extends at one side of and parallel to syringes 37. In addition to snap fastener 25 at the top of mounting bracket 26 (for retaining the lid in the closed position), bracket 26 also has a snap fastener 61 protruding inwardly toward the syringes to enable the mounting bracket to be snapped into the base portion of the casing. In addition, bracket 26 preferably has a tamper-proof prescription label base 43 for receiving, as the information displayed, an indication of the prescription for medicaments to be included in the syringes retained by the clip.

Rack 30 includes an elongated T-shaped beam, or bar, 63, the upper, horizontally extending portion 64 of which has indicator 29 at the rear edge thereof, and the lower, vertically extending portion 65 of which has teeth 67 therein at one side 68. As can be appreciated from FIGS. 3, 5 and 6, teeth 67 are relatively small and fine to better control the longitudinal movement of the beam. As shown in FIGS. 2 and 6, a series of distinguishable strips 70 are provided at side 71 of vertical portion 65 of beam 63 to sense beam positioning, as brought out more fully hereinafter.

As best shown in FIGS. 2 through 4, disposable unit 45 is inserted onto base 21 at the top 73 thereof so that the syringes 37 are received in indentions 74 as mounting bracket 26 is snapped into place centrally of the base at the front thereof.

When disposable unit 45 is snapped into position, teeth 67 of each rack 30 engage pinion, or driving, gear 76, which gear extends above top 73 of the base portion of the casing. As also shown in FIGS. 4 and 6, vertical portion 65 of beam 63 extends between driving gear 76 and a pair of guide pins 77 to constrain movement of beam 63 in opposite longitudinal directions when being driven by pinion gear 76. As also shown in FIGS. 4 and 6, optical sensor 78 is positioned adjacent to guide pins 77 (and thus adjacent to side 71 of vertical portion 65 of beam 63) to sense the positioning of the optically distinguishable strips 70 on side 71.

Each rack 30 is independently driven by a separate driving unit 80, as best shown in FIG. 6. As shown, a series of gears 81 are positioned between pinion gear 76 and stepper motor 82 (as indicated in FIGS. 6 and 13) for enabling precise movement of the rack mechanism 30. As also indicated in FIG. 6, each driving unit 80 is mounted in a separate gear box 84, which gear box is positioned within base 21 of the casing below top 73.

FIG. 7 illustrates that the pistons 48 of the plurality of syringes 37 are independently driven through separate gearing 81 and separate pinion gear 76. As shown, each gear box 84 is mounted below and in line with the path of travel of beam 63 as beam 63 drives the associated piston 48 from a retracted position (at the rear of the syringe) to an extended position (at the front of the syringe) during which movement the fluid in the syringe is expelled, or discharged, from the syringe.

A non-disposable embodiment 88 of the syringe drive device of this invention is shown in FIGS. 8 through 11. As indicated in FIG. 8, non-disposable embodiment 88 is similar to disposable embodiment 18 (as shown in FIGS. 2 through 7), except that rack 90 is mounted within the casing.

As indicated in FIG. 8, rack 90 includes indicator 29 which is visible through the slots 32 when the lid 22 of casing 19 is in the closed position (as shown in FIG. 1).

Rack 90 includes a beam, or bar, 91 having an upstanding shoulder 92 at the rear end portion (which shoulder has indicator 29 mounted at the top thereof).

As indicated in FIG. 8, beam 90 has teeth 93 on one side wall.

As shown in FIG. 9, beam 91 preferably includes a central strip 94, which strip is within outer portion 95 of the beam. The forward end 96 of outer portion 95 of beam 91 is adapted to receive tip 97, which tip engages piston 98 of syringe 100.

Tip 97 has a disc 102 thereon that has a rearwardly facing annular connector 103 extending rearwardly therefrom. Connector 103 has a lip 105 thereon, so that as connector 103 is inserted into annular groove 107 (which groove has an annular shoulder 108) at the forward end 96 of beam 91, connector 103 is snapped into the annular groove, as indicatd in FIG. 10. Alternately, the annular connector could have an inwardly directed lip which snaps over an outwardly directed shoulder on end 96 of beam 91.

A smaller disc 110 (i.e., smaller relative to disc 102) is parallel to and spaced forwardly of disc 102 by spacer 111 and terminates in guide 112 which extends forwardly of disc 110 for engaging piston 98. Disc 110 and guide 112 are inserted into piston 98 of the syringe/piston unit, as shown in FIG. 10 when the syringe is operatively positioned on the non-disposable unit. In this embodiment, only the syringe/piston unit is inserted into and removed from the syringe/piston unit.

As indicated in FIGS. 10 and 11, outer portion 95 of beam 91 can be retracted with respect to inner portion 94 to enable release of the rack from a syringe/piston unit. As shown best in FIG. 10(A), a gripping ear 114 is provided on outer portion 95 and gripping ear 115 extends extends through slot 116 so that ear 115 is connected with inner portion 94 of the beam. As the ears are moved toward one another, as indicated in FIG. 11, this causes the outer portion 95 to be retracted and pulls outer end 96 out of engagement with connector 103 of tip 97.

The driving mechanism for embodiment 88 is the same as shown in connection with the disposable unit of FIGS. 2 through 7 (i.e., pinion gear 76 meshes with teeth 96 of beam 91 to control longitudinal movement of the beam from the piston retracted position to the piston extended position, which movement of the piston effects medicament delivery from the syringe).

As indicated in FIG. 8, a cover 117 is provided for covering the pinion gears 76 and guide pins 77. While not specifically shown in FIG. 8, beam 91 preferably also has distinguishable strips 70 thereon with strip sensor 78 also being within cover 117.

A layout schematic of the syringe drive device (non-disposable or disposable) is shown in FIG. 12. As shown, a syringe pack 120 is provided (although each syringe may, if desired, be individually provided), with each syringe containing the predetermined amount of the desired medicament to be dispensed. Pack 120 (or the individual syringes) is placed in the dispensing rack (i.e., the syringes are received in indentations 74 in the top of the base portion of the drive unit) so that the drive modules 121 (i.e., the pinion gears and associated gearing to the stepper motor) drive the piston of each syringe to deliver medicament as needed. The indicators visible at the top of the unit give a visual indication of the amount of medicament delivered at any time from any syringe.

As also indicated in FIG. 12, the device is battery powered, by means of batteries 122, and preferably includes indicators (LEDs) 124 to indicate satisfactory battery charge.

As also indicated, the syringe drive unit of this invention is controlled by pre-programmed memory unit 126, which unit is preferably a programmable non-volatile logic device, such as a PROM device. It is necessary that unit 126 be inserted into the device for operation of the device. The pre-programmed memory unit is externally programmed to establish the time and amount of medicament to be delivered by each syringe and controls the operation of the drive unit so that the exact amount is independently delivered from each syringe at the exact required time.

In addition, a history 128 of medicament delivery is made and stored for use in prescribing further medicament delivery, a beeper 130 is provided for alerting purposes, and remote demand option 132 can also be provided to allow a patient to control medicament delivery when, and to the extent, allowed by the pre-programmed memory unit 126.

As indicated by the schematic of FIG. 13, a state machine 134 controls operation of stepper motor 82 through motor drive 136.

A state machine is a logic network whose output state is determined by the present state of its input and the state of data currently being read from memory. A combinational logic could be utilized in lieu of a state machine. While a microprocessor could also be utilized in lieu of a state machine, it is not preferred due to safety factors.

While only one stepper motor is illustrated in FIG. 13, it is to be realized that a separate stepper motor is provided for each rack 30 utilized. State machine 134 provides a pulse output through motor driver 136 to each stepper motor so that the drive is thus accomplished as a pulse device (rather than as a DC device). Each pulse causes the stepper motor to advance by increments, which motion is imparted through the associated gearing (within gear box 84) to pinion gear 76. As indicated in FIG. 13, a mechanical ratchet 138 is provided between stepper motor 82 and the gearing within gear box 84 to assure one-way drive. Rotation of pinion gear 76 causes longitudinal movement of beam 63 (or beam 91 if a non-disposable unit) to thus move the syringe piston a precise distance to thereby deliver the exact amount of medicament prescribed.

A stepper motor is utilized for reasons of safety in the case of an accidental conductive path forming between the power supply of the device and the motor, which with DC motors causes uncontrolled motion. A stepper motor, on the other hand, requires clearly defined pulses in order to operate. Stepper motors were not heretofore utilized for battery-operated devices, however, since one disadvantage of such motors was high power consumption.

The safety benefits of the stepper motor have been achieved by utilization of power efficient means for driving the stepper motor which has allowed use of the stepper motor without requiring high power consumption and thus has permitted use of the stepper motor with a battery operated device.

The power efficient means for operating the stepper motor is illustrated by the pulse timing llustrations of FIG. 16. The pulse timing illustrated in FIGS. 16(A) and 16(B) are manufacturer drive pulse recommendations (FIG. 16(A)), and pulses as utilized in connection with a stepper motor as reported in NASA Technical Briefs, Volume 8, No. 4, MFS-25119, Summer 1984 (FIG. 16(B)). The conventional step drive shown in FIG. 16(A) is powered on between steps and energy efficiency is low, while the drive is partially powered on between steps in the drive shown in FIG. 16(B) with energy efficiency being moderate.

FIG. 16(C) illustrates pulses in a ballistic drive utilizable in conjunction with a unidirectional rachet presenting known inertia mounted on the motor shaft and including a pawl for establishing the direction of rotation. FIG. 16(D) illustrates drive pulses that consume less energy than those previously shown in FIG. 16 and which embody a dynamic braking effect. FIG. 16(E) illustrates drive pulses allowing precise design of energy consumption and force development by the motor by means of dutycycle programming of the pulses. All of the drive pulses shown in FIGS. 16 C, D, and E can be utilized in this invention, to provide high energy efficiency, with the drive pulses as shown in FIG. 16(E) being now preferred.

The pulse parameters are chosen in view of the desired inertia presented to the motor and in view of the maximum force to be allowed for any particular application.

As also indicated in FIG. 13, an internal memory check is provided by memory check unit 140, and a clock check is provided by clock check unit 142, which unit may be connected to clocks 144 and 146. In addition, batteries 148 and 149 are connected to power the device through a diode type network 150, and a mini-battery 151 is provided for back-up. A control strip 153 is also provided for connection with the state machine.

Strip sensor 78 is positioned adjacent to side 71 of beam 63 to sense positioning of strips 70 thereon. As indicated in FIG. 13, the output of sensor 78 is provided to state machine 122. In addition, rotation of the gearing within the gear box 84 (which gearing is connected with pinion gear 76 to cause movement of the rack and syringe piston) is sensed by rotation sensor 154 (which sensing can be accomplished, for example, by placing holes in an associated gear 155 and providing a light generator at one side and a sensor 154 at the opposite side). The output from sensor 154 is also provided to state machine 122. By thus sensing longitudinal movement of the beam and gear rotation, positioning control is enhanced and verified.

An alternate embodiment 158 is shown in FIG. 14 for driving the syringe piston. As shown, a hinged rack 160 is provided to apply drive to the piston 47. To accomplish this type of drive, a plurality of rack sections 162 are provided each of which is connected with its adjacent section through a hinge pin 164. One end 166 of the thus formed hinge assembly is connected with the piston 47, and the teeth 168 on each section 162 are sequentially brought into engagement with gear 170, which gear is in engagement with worm gear 172 rotated by stepper motor 82.

In addition, while an external plug 174 is indicated, internal battery operation can be utilized in the same manner as described herein above with respect to the other embodiments described herein.

Operation is essentially the same as with the previously described embodiments, except that the driving mechanism can be adjacent to the syringe and less longitudinal space is required due to hinging of the rack.

Another drive embodiment 178 is shown in FIG. 15. As indicated, precise rotation of shaft 180 is provided by a one-way (clockwise as indicated) roller device unit 182. In this embodiment, rotation of the shaft is accomplished using balls 184 engaging the shaft. Each ball 184 is within a channel 186 having a slot 188 therein. Slot 188 is a longitudinally extending slot that is sufficiently wide to allow the ball to partly protrude there through so that the ball engages the shaft. In addition, each ball 184 is biased toward the end of the channel by a spring 190.

Clockwise rotation of the shift is permitted since the ball is being rotated by such movement in a direction away from the restraining wall of the channel. Counter-clockwise rotation of the shaft is precluded, however, since attempted rotation of the shaft in this direction forces the ball into the restraining wall of the channel. Through use of this type of drive, rotation of shaft 180 controls movement of the syringe piston and no ratchet mechanism is required.

In operation of the disposable device of this invention, the disposable unit, with a predetermined amount of medicament in each syringe to be utilized, is loaded into the drive device while the lid of the casing is in an open position, by positioning the syringes in the syringe indentations at the top of the base portion as the mounting bracket is snapped into place at the front of the base portion. When so loaded, the teeth on the rack are brought into engagement with the pinion. The casing lid is then closed and locked by the mounting bracket snapping into the lid of the casing at closing. After insertion of a pre-programmed memory unit into the casing (through a closeable aperture (not shown) in the bottom of the casing), the unit is ready for use in dispensing medicament to a patient. In use, each syringe is connected with the patient in conventional fashion and medicament is thereafter delivered to the patient under the control of the pre-programmed memory unit.

When the medicament in the syringe (or syringes) is depleted, the disposable unit is removed from the drive device and discarded. If needed, a new unit can then be placed in the drive device for continued operation. Such a new unit can contain the same or different medicaments as determined to be needed by the patient's history.

The non-disposable unit operates in essentially the same manner as does the disposable unit, except that only the syringes and pistons are introduced into the unit (either individually or as a pack) with each syringe being positioned on the base unit and each piston being then connected with a separate rack. After use, each piston is disconnected from the rack, and the syringe then taken from the base unit and discarded.

As can be appreciated from the foregoing, this invention provides an improved retaining device for positioning a receptacle, such as a syringe, to thereby enhance control of fluid delivered from the receptacle.

What is claimed is:

1. A mounting and retaining device for precise positioning of at least a first syringe adjacent to a base structure, said syringe having a syringe barrel and a syringe piston movable in said syringe barrel, and said base structure having a drive means engageable with said syringe piston, said device comprising:

a retainer mount including an upstanding wall portion, said wall portion having at least a first aperture therein having a fixed cross section, and at least a first mounting station attached to said upstanding wall portion having an arcuate wall section extending substantially perpendicularly from said upstanding wall portion adjacent to said aperture, said aperture and said arcuate wall section being configured to receive said syringe barrel of said syringe;

at least first locking means having first and second portions with said first being connected with said upstanding wall portion of said retainer mount adjacent to said mounting station and being engageable by said second portion of said locking means for releasably engaging said syringe barrel of said syringe so that said syringe barrel is substantially precluded from movement relative to said upstanding wall portion of said retainer mount; and fastening means connected with said retainer mount for releasably connecting said retainer to said base structure at a predetermined position so that a preselected orientation of said mounting station is thereby achieved and said syringe piston of said syringe is engaged by said drive means of said base structure.

2. The device of claim 1 wherein said base structure includes a plurality of drive means, wherein said upstanding wall portion of said retainer mount includes a plurality of apertures therein and a plurality of mounting stations attached thereto, and wherein a plurality of locking means are provided adjacent to said plurality of mounting stations, whereby a plurality of syringes may be positioned adjacent to said base structure so that the syringe pistons of said syringes are engaged by a different one of said plurality of drive means.

3. The device of claim 1 wherein said first portion of said locking means includes an arcuate section connected to said upstanding wall portion adjacent to said aperture, and wherein said second portion of said locking means includes an arcuate section connected to said syringe barrel of said syringe, said arcuate sections of said first and second portions of said locking means being matably engageable.

4. The device of claim 1 wherein said upstanding wall portion of said retainer mount has opposite end portions, and wherein said fastening means includes an upstanding wall section attached substantially perpendicularly to one of said end portions of said upstanding wall portion of said retainer mounts, said upstanding wall section having a snap fastener positioned thereat for releasably engaging an engageable portion located at said predetermined position of said base structure.

5. A retaining device for precise positioning of a plurality of objects adjacent to a base structure, said objects having first portions and second portions, with said second portions being movable relative to said first portions and with said direction substantially parallel to a predetermined direction of movement of said second portions relative to said first portions, and with said base structure having drive means for causing movement of said second portions of said objects relative to said first portions in said predetermined direction, said retaining device comprising:

mounting means having first and second sections with said first section extending substantially normally relative to said surfaces of said first portions of said objects and having apertures with a fixed cross section therein establishing a plurality of mounting stations having mounting surfaces extending substantially parallel to said surfaces of said first portions of said objects and configured to receive said first portions of said plurality of objects;

locking means connected with said mounting means and adjacent to said mounting stations and releasably engaging said first portions of said objects so that said first portions of said objects are substantially precluded from movement relative to said mounting means; and fastening means connected with said second portions of said mounting means for releasably connecting said mounting means to said base structure at a predetermined position so that a preselected orientation of said mounting stations is thereby achieved and said second portions of said objects are engaged by said drive means of said base structure.

6. The retaining device of claim 5 wherein said objects are syringes, wherein said second portions of said objects are syringe pistons, and wherein each of said mounting stations of said mounting means include mounting barrels having arcuate walls extending from said first section of said mounting means, each of said mounting barrels being configured to receive a different one of said syringes therethrough.

7. The retaining device of claim 5 said locking means has first and second portions with said first portion including arcuate sections adjacent to said apertures through said first section of said mounting means, and with said second portion including arcuate sections connected to said first portions of said objects, said arcuate sections of said first portions of said locking means and said arcuate sections of said second portions of said locking means being releasably engageable.

8. The retaining device of claim 5 wherein said mounting means has opposite end portions, and wherein said fastening means includes a wall section attached to one of said end portions of said mounting means substantially perpendicularly to said first section of said mounting means, said wall section having a snap fastener positioned thereat for releasably engaging an engageable portion located at said predetermined position of said base structure.

9. The retaining device of claim 8 wherein said wall section of said fastening means includes means for placing information thereon relating to said objects.

10. A disposable unit for operably positioning a plurality of syringes in a fluid delivery control device, said control device including drive means, and each of said syringes including a syringe barrel and a piston the movement of which in one direction causes ejection of fluid from said syringe barrel, said disposable unit comprising:

mounting wall means having a plurality of apertures therethrough and a plurality of mounting barrels connected thereto, said mounting barrels having arcuate walls extending substantially perpendicularly from said wall means at each of said apertures and configured to receive said syringe barrels therethrough;

bracket means attached to said mounting wall means and extending therefrom substantially parallel to said mounting barrels, said bracket means including fastening means releasably engageable with said control device at a predetermined position so that a preselected orientation of said mounting barrels of said mounting wall means is thereby achieved; and locking means connected to said wall means adjacent to said apertures for releasably engaging said syringe barrels to substantially precluded movement thereof relative to said mounting wall means.

11. The disposable unit of claim 10 further comprising a plurality of beams connectable to said pistons of said plurality of syringes, said beams having first portions engageable by said drive means of said control device upon engagement of said fastening means of said bracket means with said control device for movement of said pistons of said plurality of syringes in said one direction.

12. The disposable unit of claim 11 wherein said control device includes sensor means and wherein each of said beams have spaced strips of distinguishable material thereon, said sensor means being positioned to sense movement of said strips.

13. The disposable unit of claim 11 wherein said drive means of said control device include a plurality of pinion gears, and wherein each of said plurality of beams has teeth formed thereon for engaging a different one of said plurality of pinion gears upon engagement of said fastening means of said bracket means with said control device.

14. The disposable unit of claim 10 further comprising matable members attached to said syringe barrels of said syringes, said matable members being releasably engageable by said locking means.

15. The disposable unit of claim 14 wherein said matable members attached to said syringe barrels include arcuate lip portions and wherein said locking means includes arcuate portions adapted to receive said arcuate lip portions of said matable members, said arcuate lip portions of said matable members being rotatable to thereby lock said arcuate lip portions between said arcuate portions of said locking means and said wall means so that movement of said syringe barrels is substantially precluded.

16. A device for enhancing control of fluid flow from a plurality of syringes each of which has a piston the movement of which in one predetermined direction causes discharge of fluid from said syringe, said device comprising:
   a retaining clip having a plurality of apertures therein adapted to receive and retain said plurality of syringes in a predetermined relationship with respect to one another;
   a plurality of beams, each of which has teeth formed thereon, and each of which beams is connectable with a different one of said pistons of said syringes;
   a base unit having said retaining clip releasably mounted thereon with said base unit having a receiving portion for receiving said syringes thereon when said retaining clip is mounted on said base unit; and
   a drive unit mounted on said base unit, said drive unit having a plurality of pinion gears separately engageable with the teeth on said beams for separately driving each of said pistons in said predetermined one direction to thereby cause and control discharge of fluid from each of said syringes.

17. The device of claim 16 wherein said retaining clip, syringes, and beams are assembled as a disposable unit.

18. The device of claim 16 wherein said retaining clip includes locking means engageable with said syringes for releasably locking said syringes on said retaining clip.

19. The device of claim 18 wherein said locking means includes arcuate sections adjacent to said plurality of apertures in said retaining clip matable with arcuate sections on said syringes.

20. The device of claim 16 wherein said retaining clip includes means for placing information thereon relating to said fluid in said syringes.

* * * * *